US00PP13156P2

(12) United States Plant Patent
Heims

(10) Patent No.: US PP13,156 P2
(45) Date of Patent: Oct. 29, 2002

(54) CAMPANULA PLANT NAMED 'PINK CHIMES'

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/967,085

(22) Filed: Sep. 27, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Campanula plant characterized by a dwarf habit and pink flowers.

1 Drawing Sheet

BOTANICAL CLASSIFICATION

*Campanula punctata.*

VARIETY DENOMINATION

'Pink Chimes'.

The present invention relates to a new and distinct hybrid of *Campanula punctata*, of the family Campanulaceae, which originated from a cross between *Campanula punctata f. albiflora* 'Nana Alba' (seed parent) and *Campanula punctata* 'Cherry Bells' (pollen parent). Neither parent is patented.

The new variety has been reproduced only by asexual propagation (division and tissue culture). Each of the progeny exhibits identical characteristics to the original plant.

This plant is characterized by the following:

1. Dwarf habit.
2. Numerous large, pink flowers held over the foliage.
3. Strong flowering stems that do not fall over.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows Campanula 'Pink Chimes' in flower in a pot.

DETAILED PLANT DESCRIPTION

The following is a detailed description of the new Campanula hybrid based on observations of a one-and-a-half year old specimen grown in a two gallon pot in a cool greenhouse in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—30 cm. wide and 12 cm. tall.
- *Form.*—Basal clump.

Leaf:
- *Type.*—Simple.
- *Shape.*—Ovate-cordate.
- *Arrangement.*—Rosette.
- *Length.*—5 cm.
- *Width.*—3 cm. at the widest part.
- *Margins.*—Doubly serrate, undulate.
- *Apex.*—Acuminate.
- *Base.*—Cordate.
- *Texture.*—Sparsely hispid on the topside and hispid on the bottom.
- *Petiole length.*—13 cm., clasping at the base.
- *Petiole texture.*—Hispid.
- *Petiole color.*—Greyed Orange 177B to 187B.
- *Venation.*—Pinnate.
- *Color.*—Topside — Green 137B. Bottom — Green 138B with margins darker, Greyed Purple 187B..

Inflorescence:
- *Type.*—Terminal panicle.
- *Peduncle.*—Height: 12 to 35 cm. Diameter: 0.2 cm. at widest. Texture: Hispid. Color: Yellow Green 144A, sometimes in the sun there is an overlay of maroon, Greyed Purple 187A.
- *Pedicel.*—Length: 0.9 cm. Texture: Hispid. Color: Yellow Green 144A.
- *Flower number.*—Approximately 8 to 16 per panicle.

Flower bud:
- *Size.*—2.5 to 5.5 cm. deep and 1 to 2 cm. wide.
- *Shape.*—Ovoid, pentagonal in cross section.
- *Color.*—Closest to Red Purple 59B.
- *Texture.*—Sparsely scabrous on veins.

Flower:
- *Type.*—Actinomorphic.
- *Shape.*—Campanulate.
- *Size.*—4 to 6 cm. deep and 2 to 2.5 cm. wide.
- *Corolla.*—Inflated tube with 5 acute lobes that reflex back at tips. Lobes are 1.2 cm deep and 1.2 cm wide at the base.
- *Texture.*—Sparsely scabrous on veins and villous on lobe margins.
- *Color.*—Appearing pink due to a heavily speckled overlay of Red Purple 70A on outside and inside White 55B spotted with Red Purple 70A with the heaviest spotting at the veins.
- *Calyx.*—5 deeply cut acuminate lobes, ovate lanceolate, parted ⅔ to base, with basal lobes reflexed all the way back to the pedicel.

*Calyx size.*—2.3 cm deep and 2 cm wide.
*Calyx color.*—Yellow Green 144A (Greyed Orange 177A in bright sun).
*Pistil.*—2.2 cm. long, White 155A, stigma 3-parted.
*Stamen number.*—5.
*Filament length.*—0.4 cm.
*Anther size before dehiscing.*—0.8 cm.
*Pollen color.*—Yellow 4D.
*Bloom period.*—May through July in Canby, Oreg. It will rebloom when cut back if climates are mild.
*Fragrance.*—None.

Fruit:
*Type.*—3-celled capsule.
*Color.*—Tan, Grey Brown 199D.

Seed:
*Color.*—Grey Brown 199A.
*Size.*—Approximately 1 mm. long.
*Shape.*—Oval.
*Fertility.*—Fertile.

Disease: None observed on plant grown under commercial conditions in Canby, Oreg.

COMPARISONS TO SIMILAR CAMPANULA

Compared to *Campanula punctata* 'Cherry Bells', an unpatented plant, this new cultivated variety has a dwarfer habit, better suited to potted plant culture.

Compared to *Campanula punctata* 'Bowl of Cherries' (Plant patent application Ser. No. 09/967,087, filed Sep. 27, 2001), this new cultivated variety has the appearance of pink flowers rather than deep red purple flowers.

I claim:

1. A new and distinct hybrid of Campanula plant substantially as shown and described, characterized by a dwarf habit and pink flowers.

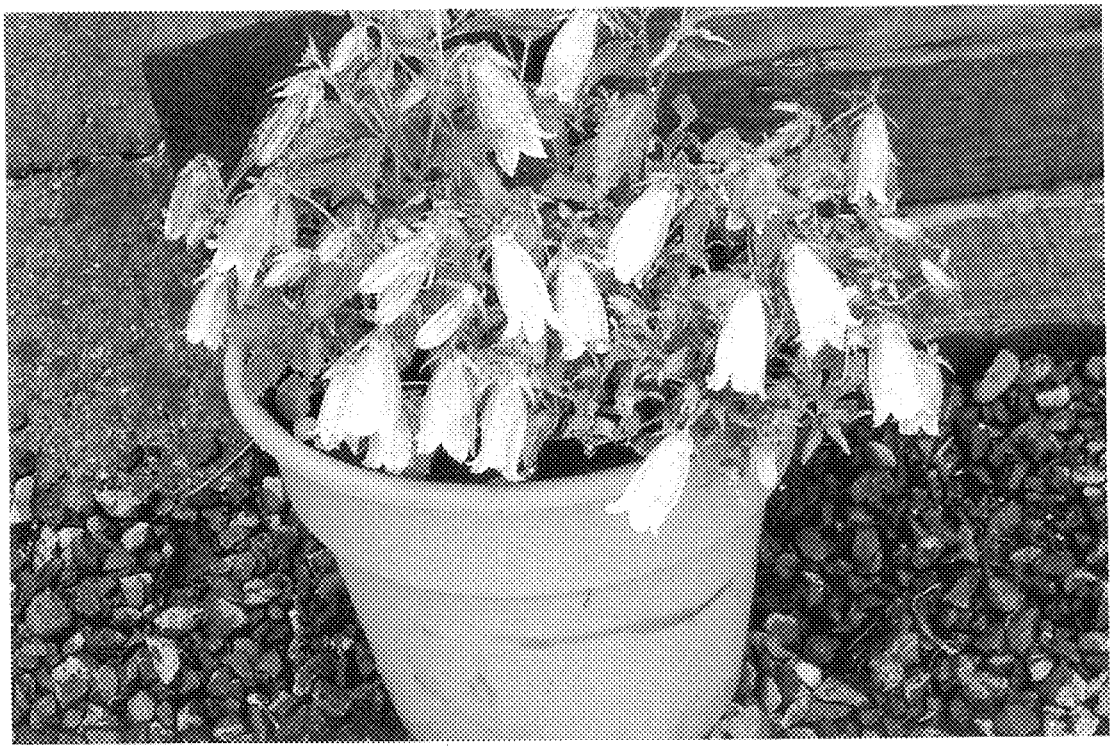

* * * * *